United States Patent [19]

Lindquist

[11] 4,136,388

[45] Jan. 23, 1979

[54] DATA ACQUISITION SYSTEM FOR COMPUTED TOMOGRAPHY

[75] Inventor: Thomas R. Lindquist, Oxford, Conn.

[73] Assignee: U.S. Philips Corporation, New York, N.Y.

[21] Appl. No.: 827,932

[22] Filed: Aug. 26, 1977

[51] Int. Cl.² .................................................. G01N 23/00
[52] U.S. Cl. .................................. 364/414; 250/445 T; 364/577
[58] Field of Search ............... 364/414, 572, 527, 577, 364/515; 250/445 R, 445 T, 362, 350

[56] References Cited

U.S. PATENT DOCUMENTS

| | | | |
|---|---|---|---|
| 3,748,470 | 7/1973 | Barrett | 250/320 X |
| 3,755,672 | 8/1973 | Edholm et al. | 250/322 |
| 4,002,911 | 1/1977 | Hounsfield | 250/445 T X |
| 4,032,761 | 6/1977 | Mayo et al. | 250/445 T X |
| 4,052,619 | 10/1977 | Hounsfield | 250/445 T X |

*Primary Examiner*—Edward J. Wise
*Attorney, Agent, or Firm*—Thomas A. Briody; Jack E. Haken

[57] ABSTRACT

The radiation source and detectors in a computed tomography system translate and/or rotate with varying velocity profiles. Radiation transmission data is measured and sampled at a high rate, the sample points being equally spaced in the time domain. The data samples are then smoothed and interpolated, using a high order polynomial fit, to provide input signals for an image reconstruction algorithm which are representative of transmission values at points which are evenly distributed in space.

16 Claims, 3 Drawing Figures

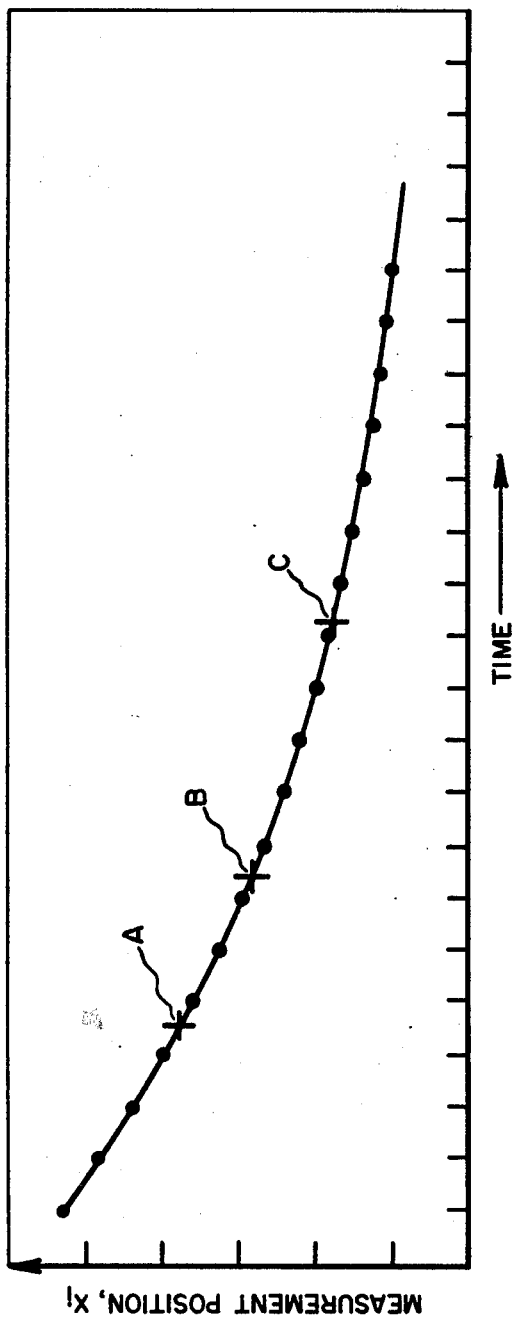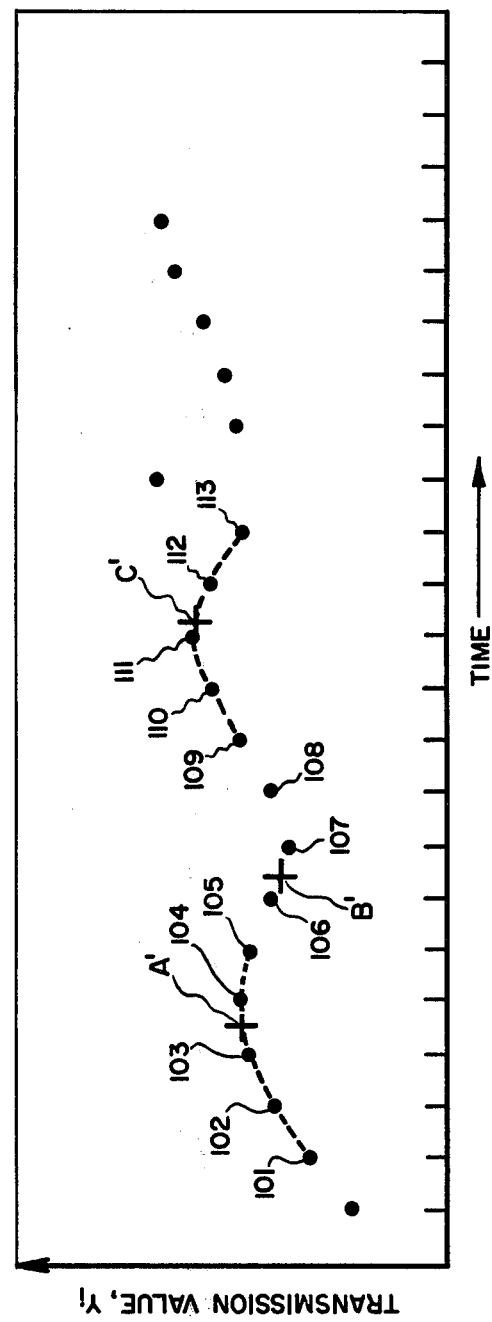
Fig. 2
Fig. 3

DATA ACQUISITION SYSTEM FOR COMPUTED TOMOGRAPHY

This invention relates to radiation measurement and signal processing systems for use with computed tomography (CT) imaging equipment.

BACKGROUND OF THE INVENTION

Apparatus for examining objects by means of penetrating radiation, typically X-ray or gamma-ray radiation, and for producing cross-section images thereof by the methods of computed tomography is well known and is described, for example, in U.S. Pat. No. 3,778,614 to Hounsfield. In typical CT apparatus the object undergoing X-ray examination is scanned by an X-ray source in combination with one or more X-ray detectors which rotate and/or translate about the object to measure radiation transmission along a large plurality of independent paths in an examination plane. Data obtained from the detectors is then processed and combined, typically by using well known computational algorithms in a digital computer, to generate images of transmissivity characteristics in the plane.

Several computational algorithms are available for generating image information from transmission data. A convolution and backprojection algorithm, of the type first described by Ramachandran and Hakshminarayanan, is generally believed to provide a reasonable compromise between computer equipment cost and image reconstruction time and is utilized, in various forms, in most CT equipment presently in commercial production. Convolution-backprojection algorithms of this type are most efficiently utilized with transmission data measured at discrete points which are uniformly distributed in space. However, the scanning mechanisms which are utilized in the measurement of radiation transmission generally comprise large, high inertia components and tend to translate and/or rotate with time-varying velocity profiles. When data from such mechanisms is sampled at a uniform periodic rate the corresponding transmission paths are not uniformly distributed in space.

SUMMARY OF THE INVENTION

In accordance with the present invention, measurements of X-ray transmission in CT apparatus are made at points which are equally spaced in time (and which are generally not equally distributed in space) at a sampling rate substantially higher than the cut-off frequency of the filter function utilizied in a convolution-backprojection image reconstruction algorithm. Groups of data samples which surround each of a series of points (uniformly distributed in space) are fitted to a high order curve, typically a quadratic curve, which is interpolated to calculate equivalent data signals having a uniform spatial distribution. The system allows data acquisition at a uniform rate, which generally reduces hardware cost and complexity; inherently provides low pass filtering to reduce noise, and allows effective multiplexing and transmission of data from the scanning apparatus to the digital computer.

It is, therefore, an object of this invention to reduce the complexity of scanning and data transmission apparatus in computed tomography systems. Another object of this invention is to reduce the effect of statistical signal variations and noise on the image quality in computed tomography systems.

BRIEF DESCRIPTION OF THE DRAWINGS

The novel features believed to be characteristic of the present invention are set forth in the appended claims. The invention itself, together with further objectives and advantages thereof, may best be understood with reference to the following detailed description, taken in connection with the appended drawings in which:

FIGS. 2 and 3 graphically describe the data sampling methods and operations of the present invention.

DESCRIPTION OF THE PREFERRED EMBODIMENTS

Figure 1:
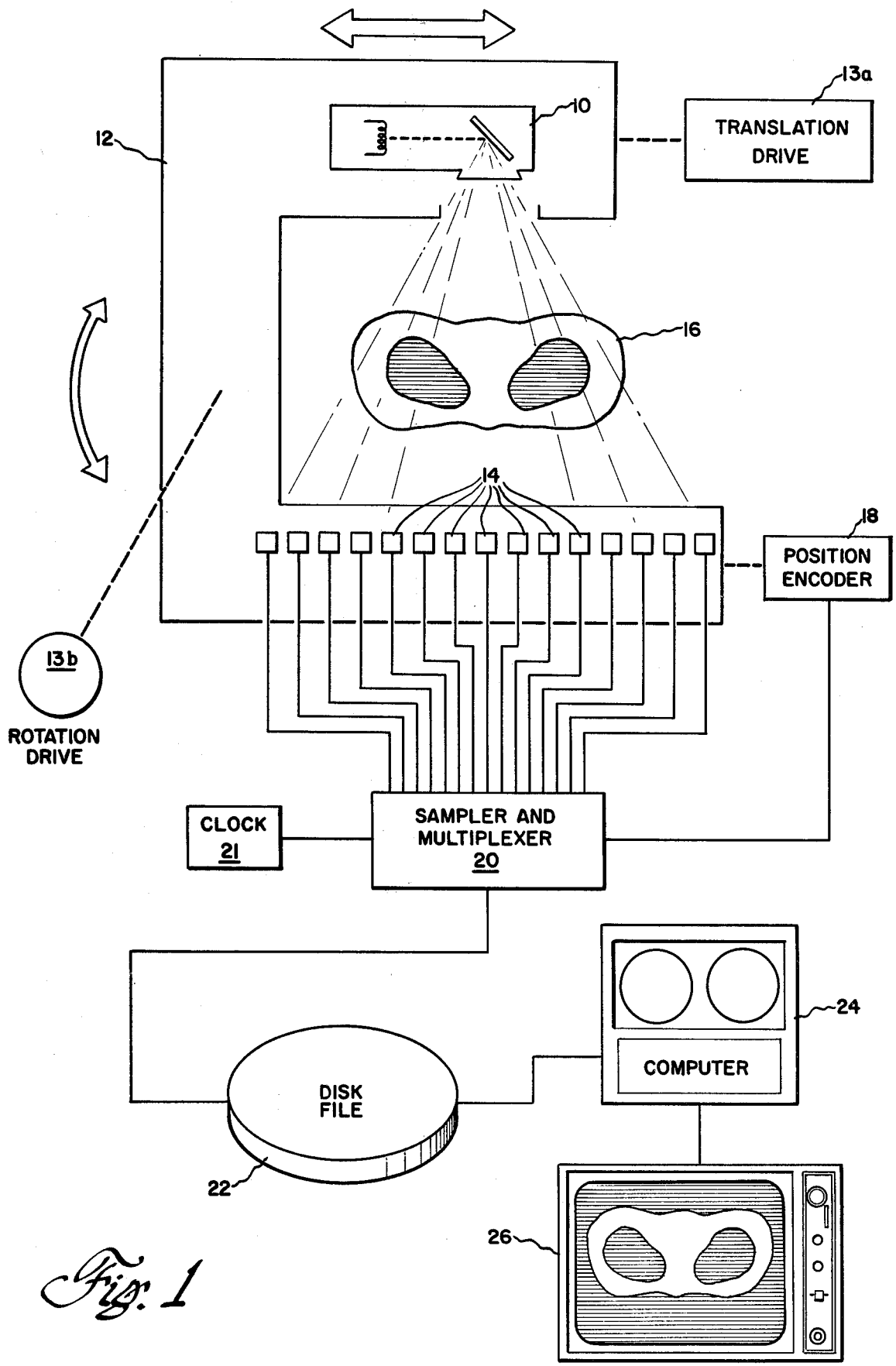
FIG. 1 schematically represents a computed tomography system of the present invention.

FIG. 1 is a computed tomography system which may incorporate the data processing equipment and techniques of the present invention. An X-ray or other radiation source 10 is mounted on a yoke 12 opposite a linear array of radiation detectors 14. An object 16 undergoing tomographic examination is disposed between the radiation source 10 and the detectors 14 in the path of radiation propagating therebetween. Motor drive 13a and 13b cause the yoke 12 to translate and/or rotate about the object 16 whereby the detectors 14 produce signals which are representative of the radiation intensity transmitted from the source 10 to the detectors 14 along a large number of separate paths through the object 16.

A position encoder 18 is connected between the yoke 12 and a fixed reference to produce signals which are representative of the rotational and translational position of the source and detectors with respect to the body 16. Signals from the individual detectors 14 and the position encoder 18 are periodicly sampled and combined, typically in digital form, in a sampler and multiplexer circuit 20 and are typically stored, for example in a disk file 22 and transmitted to a digital computer 24 which generates image data representative of the physical characteristics of the object 16. The image data may, typically, be displayed on a cathode ray tube display 26 which is driven by the computer 24.

In general the yoke 12 will undergo some velocity changes while X-ray measurements are being taken. Such changes may be necessary, as in the case where acceleration and deceleration must take place near the ends of translational motion where ray measurements are still required. Other changes may be unintentional but difficult to avoid due to the performance limitations of the yoke velocity control system. Thus the velocity of the yoke may vary substantially as it rotates and/or translates about the object 16. If the multiplexer circuit 20 operates to acquire data from the detectors 14 at a uniform periodic rate; the data thus obtained will represent radiation transmission along paths which are non-uniformly distributed in space. Such data is, generally, not suited for economical image reconstruction with a convolution-backprojection algorithm.

Image reconstruction algorithms may compute the radiation absorption at each of a large number, N, of picture elements by solution of an equal or larger number of simultaneous equations with N unknown values. A minimum of N X-ray transmission data points must, therefore, be obtained to allow a closed solution of the set of image equations. In accordance with the present invention radiation transmission data is measured by the detectors 14 over a substantially larger number of transmission paths (typically 5-10 times as many paths) than the number of desired picture elements in the computed image. The position of the yoke 12, which is in continuous motion during the course of the measurements, is monitored during the measurement process and is stored, along with the values of the detector 14 signals on the disk file 22. In a typical system the multiplexer 20 serially scans an array of detectors 14 (which may, for example, include 30 separate detectors) and samples the position encoder twice during each scan of the detector signals.

Signals representative of the sampled signals from the detectors 14 and of the corresponding position of the yoke 12 are received by the digital computer 24 from the disk file 22 and are processed by a program (an example of which is included as Appendix A) which compensates for the geometry and motion of the yoke and detector array to produce a data file representative of the actual spatial position of the transmissivity measurements with respect to known reference points in the scanner mechanism. The curves in FIGS. 2 and 3 represent typical data which might be produced by those measurements and computations. The round dots in the Figures represent data values which are transmitted by the multiplexer 20 to the disk file 22 at uniform intervals in time. FIG. 2 represents the spatial position of each of the computed measurement points which, because of the non-uniform motion of the yoke 12, are not uniformly distributed in space. FIG. 3 represents corresponding transmission values obtained at each of the data points which values vary as a function of the structure of the object 16 and which are also subject to statistical variation and the effects of additive noise. Points A, B and C in FIG. 2 represent the position of a set of uniformly distributed measurement paths which define desirable measurement points for data input to a convolution-backprojection image reconstruction program. The corresponding points A', B' and C' in FIG. 3 represent equivalent sample times at which optimum data sampling for the paths A, B and C are desired. Typically, the points A', B' and C' do not correspond with the actual sampled data points.

In accordance with the present invention, transmission data values from a group of sample points adjacent the optimum measurement positions A', B' and C' are interpolated to provide an equivalent transmission value at the optimum measurement positions A', B' and C'. For example, the equivalent transmission value $Y_A$ at the point A' is calculated by interpolating measured transmission values at the five nearest sample points 101, 102, 103, 104 and 105. Likewise the equivalent transmission value at the point C', $Y_C$, is determined by interpolating data from the five nearest measurement points 109, 110, 111, 112 and 113.

Interpolation is most efficiently accomplished in the digital computer. The computer program first searches the file of position encoder values, as corrected for scanner geometry and motion effects, to determine which measurement point is closest in space to the effective position of a desired transmission path. The closest measurement point (for example point 103 for path position A') together with the four adjoining measurement points (101, 102, 104 and 105) are fitted to a curve, typically a quadratic or higher order curve, by means of a leastsquares fitting technique, or any other accepted method, to produce a functional representation of the continuous variation of transmission values in the region of the point A'. The generated function is then interpolated to provide an equivalent transmission value at the point A'. The curve fitting and interpolation algorithm provides smoothing of statistical data variations, in effect providing a low pass filer, and allows optimum spacing of equivalent transmission paths for efficient use of the convolution-backprojection algorithm.

By way of example a quadratic curve having the form $a + bx + cx^2$ may be generated through the points $y_{-2}...y_2$ by a least-squares quadratic fit using the equations $$a = 1/35(-3y_{-2} + 12y_{-1} + 17y_0 + 12y_1 - 3y_2)$$

$$b = 1/10(-2y_{-2} - y_{-1} + y_{1+2}\,y_2)$$

$$c = 1/10 \left[ \sum_{i=-2}^{2} y_i - 5a \right]$$

This curve is then interpolated to produce data at equivalent points which are most suited for use in a reconstruction algorithm, for example a convolution-backprojection algorithm based on the method of Ramachandran and Lakshinarayanan.

By way of further example and to permit others to more easily practice the invention Appendix A is a representative computer program (written in Digital Electronics Corporation PDP 11 machine language with Fortran subroutines) which compensates for scanner motion and geometry effects and synthesizes optimal spatially sampled data from uniformly time sampled data.

The methods and apparatus of the present invention allow rapid scanning and acquisition of transmission data for computed tomography systems, by permitting use of scanning mechanisms having non-uniform velocity profiles, with subsequent efficient processing using convolution-backprojection algorithms. The method further allows statistical averaging and low-pass filtering which tend to reduce the effects of noise and other statistical variations on image quality and thus contribute to lower radiation levels and patient dose.

The invention has been described in detail herein in accord with certain embodiments thereof, yet many modifications and changes may be effected by those skilled in the art. Accordingly, it is intended by the appended claims to cover all such modifications and changes as fall within the true spirit and scope of the invention.

APPENDIX "A"

```
;TASK WHICH CREATES PROJECTIONS (G(L,THETA)) FROM RAW SCAN DATA
;
;COPYRIGHT 1976 BY PHILIPS MEDICAL SYSTEMS, INC.

;RAW DATA STARTS A  RDSSEC ON DK1:
;G DATA STARTS AT  SSEC ON DK1:  (MAY OVERWRITE RAW DATA)
;THIS PROGRAM DOES THE FOLLOWING:
;         READS TIME-SAMPLED DATA FROM DISK
;         FINDS SYNC
```

```
;       CONVERTS NUMBERS FROM DATA ACQUISITION ELECTRONICS TO MU SUMS
;       SYNTHESIZES SPATIALLY SAMPLED DATA FROM TIME SAMPLED DATA
;       WRITES 1 G TO DISK FOR EACH DETECTOR FOR EACH TRANSLATION
;
;THE RAW DATA CONSISTS OF FRAMES OF 34 WORDS EACH, IN THE FORM:
;       SYNC            ALWAYS 0
;       POSITION        LINEAR ENCODER READING
;       DETECTOR 1      1ST DETECTOR IN DETECTOR ARRAY
;       DETECTOR 2      2ND
;       ETC.
;       DETECTOR 15
;       REF. DETECTOR   SIGNAL FROM REFERENCE DETECTOR
;       POSITION        ANOTHER LINEAR ENCODER READING
;       DETECTOR 16
;       DETECTOR 17
;       ETC.
;       DETECTOR 30
;
;THE DETECTOR READINGS ARE THE OUTPUT OF A LOGARITHMIC AMPLIFIER.
;THE G ARRAYS ARE 512 WORDS LONG, OF WHICH THE 1ST 511 ARE DATA
;
        .GLOBL  MG
        .LIST   MEB
        .MCALL  QIOSS,WTSESS,EXITSS,RQSTSS
        .MCALL  FSRSZ$,FDBDF$,FDRC$A,FDOP$A
        .MCALL  NMBLK$,CLOSES,OPEN$R,GET$S
        .MCALL  ALUN$S
;
        SY0=1
        DK1=2
        LGREC=512.
        NSPSAM=511.
        RDSSEC=24.
        GSSEC=24.
        SEXIBF=12.
        NDETS=30.
        FANANG=10000.
        SAXDMM=4445.
        ENCLPI=2009.
        AMICRO=700.
        NTRANS=18.
        BYTSIB=2*SEXIBF*256.
        BYTSOB=2*NDETS*LGREC
        SXPTRN=11.*24.
        BFSTRN=SXPTRN/SEXIBF
        OSXTRN=NDETS*LGREC/256.
        NFRMS=2*BYTSIB/68.-14.
        NFRPB=BYTSIB/68.+1
        IDIFSH=7
        TAU=18.
        TN=5

;
;MACRO TO TEST FOR I/O ERRORS
        .MACRO  TST1OS  SB
        CMPB    SB,#IS.SUC      ;TEST FOR SUCCESSFUL I/O
        BEQ     1$
        JSR     PC,ERR          ;ABORT IF I/O WAS BAD
1$:                             ;CONTINUE
        .ENDM   TST1OS
;
;MACRO TO MULTIPLY AND ADD TO ACHI,ACLO
        .MACRO  MAS     FACT1,FACT2
        MOV     FACT1,R4
        MUL     FACT2,R4
        ADD     R5,ACLO
        ADC     R4
        ADD     R4,ACHI
        .ENDM   MAS
;
;
        FSRSZ$  1,512.

FDBIDN: FDBDF$
        FDRC$A  ,RCPBUF,512.
        .WORD   RCPBUF
        .WORD   512.
        FDOP$A  SY0,,IDNNAM
        .BYTE   SY0
        .WORD   IDNNAM
;
IDNNAM: NMBLK$  RECP,DAT
        .RAD50  /RECP/
        .WORD   0
        .RAD50  /DAT/
;
;
;
MG:     CLR     TRNSDN
        MOV     #GSSEC,OUTSEC   ;AND OUTPUT SECTOR
;
;READ SCAN PARAMETERS FROM DISK FILE CREATED BY SETREC
        MOV     #FDBIDN,R0      ;MOVE FDB ADDRESS INTO R0
REDWDS: OPEN$R  R0,,,,,ERR      ;OPEN RECP.DAT FILE FOR READING
        .IIF    NB,#FO.RD,      MOVB #FO.RD,F.FACC(R0)
        JSR     PC,.OPEN
        BCC     .+6
        JSR     PC,ERR
```

```
GETDT:  GETSS   R0,,,ERR            ;READ THE DATA INTO RCPBUF
        JSR     PC,.GETSQ
        BCC     .+6
        JSR     PC,ERR
        MOV     #RCPBUF+2,R1
        MOV     (R1)+,IA
        MOV     (R1)+,IOFF
        MOV     (R1)+,ISA
        MOV     (R1)+,TAUSF
        MOV     (R1)+,FACTOR
        MOV     (R1)+,NOISLM
        MOV     (R1)+,DPLIM
        MOV     (R1)+,IFA
        MOV     (R1)+,ITO
        CLOSES  R0,ERR
        JSR     PC,.CLOSE
        BCC     .+6
        JSR     PC,ERR
;
;COMPUTE NORMALIZATION FACTOR FROM (POSSIBLY PATCHED) VALUE OF A:
        CLR     R4
        MOV     FACTOR,R5
        ASHC    #9.,R4
        DIV     IA,R4               ;FACTOR*1000/IA
        MOV     R4,SCFAC
;
;SET UP TABLES OF DETECTOR PARAMETERS:
;COMPUTE TABLE OF ENCODER READINGS CORRESPONDING TO L=0
;AND
;COMPUTE TABLE OF DIFFERENTIAL ENCODER READINGS
;
;CALL CETABS(IA,IOFF,ISA,IFA,ITO,ND,LPI)
        MOV     #ARGLST,R5
        JSR     PC,CETABS
;
;SELECT # OF POINTS TO BE SMOOTHED
ASK:    QIO$S   #IO.WLB,#TM,#1,,#IOSTB,,<#PMSG,#2,#0>
        CLR     -(SP)
        CLR     -(SP)
        CLR     -(SP)
        CLR     -(SP)
        MOV     #2,-(SP)
        MOV     #PMSG,-(SP)
        CLR     -(SP)
        MOV     #IOSTB,-(SP)
        CLR     -(SP)
        MOVB    #1,(SP)
        MOV     #TM,-(SP)
        MOV     #IO.WLB,-(SP)
        MOV     (PC)+,-(SP)
        .BYTE   1,12.
        EMT     ^O<377>
        WTSE$S  #1
        MOV     #1,-(SP)
        MOV     (PC)+,-(SP)
        .BYTE   41.,2
        EMT     ^O<377>
        CMPB    #IS.SUC,IOSTB
        BEQ     1$
        JSR     PC,ERR
1$:     QIO$S   #IO.RLB,#TM,#1,,#IOSTB,,<#SMOTH,#2>
        CLR     -(SP)
        CLR     -(SP)
        CLR     -(SP)
        CLR     -(SP)
        MOV     #2,-(SP)
        MOV     #SMOTH,-(SP)
        CLR     -(SP)
        MOV     #IOSTB,-(SP)
        CLR     -(SP)
        MOVB    #1,(SP)
        MOV     #TM,-(SP)
        MOV     #IO.RLB,-(SP)
        MOV     (PC)+,-(SP)
        .BYTE   1,12.
        EMT     ^O<377>
        WTSE$S  #1
        MOV     #1,-(SP)
        MOV     (PC)+,-(SP)
        .BYTE   41.,2
        EMT     ^O<377>
        CMPB    #IS.SUC,IOSTB
        BEQ     2$
        JSR     PC,ERR
2$:
        MOV     SMOTH,R1
        CMP     #65,R1
        BNE     3$
        MOV     #5,SMOTH
        MOV     #0,DISP
        BR      DOTRAN
3:      CMP     #31461,R1
        BNE     4$
        MOV     #13.,SMOTH
        MOV     #10.,DISP
        BR      DOTRAN
```

```
8:      CMP     #71,R1
        BNE     .ASK
        MOV     #9.,SMOTH
        MOV     #28.,DISP

PROCESS DATA OF 1 TRANSLATION:
OTRAN:  CLR     BFSRQD          ;0 BUFFERS REQUESTED
;QUEUE INPUT REQUEST FOR DATA INTO 1ST 2 INPUT BUFFERS
        MOV     TRNSDN,R1
        MUL     #SXPTRN,R1
        ADD     #RDSSEC,R1
        MOV     R1,INPSEC
        QIO$S   #IO.RLB,#DK1,#2,,#SB2,,<#IB1,#2*BYTSIB,,#0,INPSEC>,ERR
        CLR     -(SP)
        MOV     INPSEC,-(SP)
        CLR     -(SP)
        CLR     -(SP)
        MOV     #2*BYTSIB,-(SP)
        MOV     #IB1,-(SP)
        CLR     -(SP)
        MOV     #SB2,-(SP)
        CLR     -(SP)
        MOVB    #2,(SP)
        MOV     #DK1,-(SP)
        MOV     #IO.RLB,-(SP)
        MOV     (PC)+,-(SP)
        .BYTE   1,12.
        EMT     ^O<377>
        BCC     .+6
        JSR     PC,ERR
        ADD     #2,BFSRQD
        ADD     #2*SEXIBF,INPSEC
;QUEUE INPUT REQUEST FOR 3RD INPUT BUFFER FILL
        QIO$S   #IO.RLB,#DK1,#3,,#SB3,,<#IB3,#BYTSIB,,#0,INPSEC>,ERR
        CLR     -(SP)
        MOV     INPSEC,-(SP)
        CLR     -(SP)
        CLR     -(SP)
        MOV     #BYTSIB,-(SP)
        MOV     #IB3,-(SP)
        CLR     -(SP)
        MOV     #SB3,-(SP)
        CLR     -(SP)
        MOVB    #3,(SP)
        MOV     #DK1,-(SP)
        MOV     #IO.RLB,-(SP)
        MOV     (PC)+,-(SP)
        .BYTE   1,12.
        EMT     ^O<377>
        BCC     .+6
        JSR     PC,ERR
        INC     BFSRQD
        ADD     #SEXIBF,INPSEC
        MOV     TRNSDN,R5
        INC     R5
        JSR     PC,CONV2D       ;STORE ASCII T## IN MESSAGE BUFFER
        MOV     R5,MES0
;WAIT FOR 1ST 2 BUFFERS TO FILL
        WTSE$S  #2
        MOV     #2,-(SP)
        MOV     (PC)+,-(SP)
        .BYTE   41.,2
        EMT     ^O<377>
;
;
EF2:
;CHECK FOR I/O ERROR
        TSTIO$  SB2
        CMPB    SB2,#IS.SUC     ;TEST FOR SUCCESSFUL I/O
        BEQ     1$
        JSR     PC,ERR          ;ABORT IF I/O WAS BAD
;ESTABLISH SYNC IN IB1
        MOV     #IB1,R4
        JSR     PC,FSYNC
;
;DETERMINE WHETHER GOING L-R OR R-L
        MOV     2(R4),R0        ;GET A POSITION WORD
        NEG     R0              ;NOP FOR SIMULATOR ****************
        SXT     LTOR
        INC     LTOR            ;LTOR=1 IF GOING L TO R
        MOV     LTOR,LINC
        BGT     CONT
        DEC     LINC            ;INCREMENT L BY +OR-1
CONT:
;(RIGHT IS DEFINED WITH DETECTORS AT BOTTOM,LOOKING FROM FEET)
;
;NOW IS GOOD TIME TO SAVE BASE LINE READINGS FROM ALL DETECTORS
;
;CONVERT IB1 DETECTOR READINGS TO MU SUMS
        MOV     #IB1,R4
;ESTABLISH SYNC IN IB2
        MOV     #IB2,R4
        JSR     PC,FSYNC
;CONVERT IB2 DETECTOR READINGS TO MU SUMS
;
;INITIALIZE LDUN ARRAY TO 0'S IF GOING LEFT-TO-RIGHT;
```

```
;INITIALIZE TO 512'S IF GOING RIGHT-TO-LEFT.
        MOV     #LDUN,R0
        MOV     #NDETS,R1
        MOV     LTOR,R3
        NEG     R3
        INC     R3
        MUL     #NSPSAM+1,R3
CLDNLP: MOV     R3,(R0)+
        SOB     R1,CLDNLP
        MOV     LTOR,R3
        MUL     #NSPSAM-1,R3
        INC     R3              ;SET LDNLIM=1 OR 511
        MOV     R3,LDNLIM
;
DECOM:
;DECOMMUTATE AND FIT INTO SPATIAL INTERVALS FOR AS MANY L'S AS CAN
;
        CLR     IDET
        MOV     #IB1,R4
        JSR     PC,FSYNC
        ADD     #7*68.,R4
        ADD     #2,R4
        MOV     R4,FRSTPO
        ADD     #NFRMS-1*68.,R4
        MOV     R4,LASTPO
        MOV     @LASTPO,R1
        SUB     @FRSTPO,R1
        SXT     R0
        DIV     #NFRMS-1,R0     ;COMPUTE AVERAGE VELOCITY******
        MOV     R0,DENCPF       ;CHANGE IN ENCODER READING/FRAME
        ASR     R0
        MOV     R0,HAFDEN       ;1/2 THE ENCODER READING CHANGE/FRAME
        SUB     #2,R4
        TST     (R4)            ;STILL IN SYNC NEAR END OF IB2?
        BEQ     CKSYN
        HALT                    ;NO.****************************
CKSYN:  MOV     #NFRPB,R2
        MOV     FRSTPO,R1
        SUB     #2,R1
        MOV     SPACES,MES1
        MOV     YN,MES2
CSLOOP: TST     (R1)
        BEQ     SYNCOK          ;CHECK FOR SYNC=0
        MOV     #MES3,R3
        MOV     (R1),R5         ;PRINT SYNC, ENCODER
        JSR     PC,OCTASC
        MOV     #MES4,R3
        MOV     2(R1),R5
        JSR     PC,OCTASC
        JSR     PC,PRINT
SYNCOK: ADD     #68.,R1
        SOB     R2,CSLOOP
;
CKENC:  MOV     #NFRPB,R2
        MOV     FRSTPO,R1
        ADD     #68.,R1
        MOV     SPACEE,MES1
        MOV     NC,MES2
CELOOP: MOV     68.(R1),R5
        SUB     (R1),R5
        ADD     -68.(R1),R5
        SUB     (R1),R5
        BPL     10$
        NEG     R5
10$:    SUB     ACLIM,R5        ;COMPARE ACCEL WITH LIMIT
        BLT     ENCOK
        MOV     #MES3,R3
        MOV     (R1),R5         ;PRINT ENCODER, ENCODER
        JSR     PC,OCTASC
        MOV     #MES4,R3
        MOV     34.(R1),R5
        JSR     PC,OCTASC
        JSR     PC,PRINT
ENCOK:  ADD     #34.,R1
        SOB     R2,CELOOP
;
CKDETS: MOV     FRSTPO,R1
        ADD     #2,R1
        MOV     R1,FRSTD
        MOV     SPACED,MES1
        MOV     #1,DET
CKIDET: MOV     FRSTD,R1
        MOV     DET,R5
;                               STORE ASCII D## IN MESSAGE BUFFER
        JSR     PC,CONV2D
        MOV     R5,MES2
        MOV     #NFRPB,R2
CKDTLP: MOV     68.(R1),R5
        SUB     (R1),R5
        BPL     20$
        NEG     R5              ;CHECK FOR DET DISCONT > NOISLM
20$:    SUB     NOISLM,R5
        BLT     DOK
        MOV     #MES3,R3
        MOV     (R1),R5         ;PRINT DET, DET
        JSR     PC,OCTASC
        MOV     #MES4,R3
        MOV     68.(R1),R5
        JSR     PC,OCTASC
        JSR     PC,PRINT
```

```
DOK:      ADD     #68.,R1
          SOB     R2,CKDTLP
          INC     DET
          ADD     #2,FRSTD
          CMP     DET,#16.
          BLT     CK1DET
          BCT     30S
          ADD     #4,FRSTD
30S:      CMP     DET,#31.
          BLT     CK1DET
;
DOADET:   MOV     IDET,R0
          ASL     R0
          MOV     TAUSF,R4         ;COMPUTE CORRECTION FOR SAMPLE
;                                      TIME OFFSET
          SUB     DOFFT(R0),R4
          MUL     DENCPF,R4
          DIV     #34.,R4
          MOV     R4,ENCADJ        ;(DENCPF*(TAUSF-DOFF(IDET))/34.
          MOV     FRINDT(R0),R1    ;GET BYTE OFFSET FOR CURRENT DETECTOR
          MOV     LDUN(R0),LTRY    ;ARE ALL 511 VALUES COMPUTED?
          BPL     CONDOD           ;NO
          JMP     BMPIDT           ;YES
CONDOD:   ADD     LINC,LTRY        ;NO. TRY TO COMPUTE ANOTHER
          MOV     IDET,R5
          MUL     #LGREC*2,R5
          ADD     #OB,R5
          MOV     R5,CURGAD
          MOV     FRSTPO,R3        ;INITIALIZE SEARCH POINTER
          MOV     NCANDS,R2        ;AND COUNTER
;
;
;
;COMPUTE NOMINAL ENCODER VALUE FOR THIS DET FOR CURRENT LTRY
CMPNOM:   MOV     LTRY,R4
          SUB     #NSPSAM+1/2,R4   ;LTRY-256
          MUL     IDIF(R0),R4      ;ENCODER OFFSET FROM CENTER
          ASHC    #-IDIFSH,R4
          ADD     ICEN(R0),R5      ;NOM. ENC. VALUE = VALUE(256) +
;                                      SLOPE*(LTRY-256)
          NEG     R5               ;NOP FOR SIMULATOR *****************
          ADD     ENCADJ,R5        ;COMPENSATE FOR TIME OFFSET
          MOV     R5,ENCNOM
;SCAN FORWARD IN IB1,IB2 LOOKING FOR ENCNOM
SRCHFW:
CKLTOR:   TST     LTOR             ;MOVING LEFT-TO-RIGHT?
          BNE     SBWLP            ;BEQ FOR SIMULATOR *****************
SFWLP:    CMP     (R3),ENCNOM
          BCC     PASTIT
          ADD     #68.,R3
          SOB     R2,SFWLP
          JMP     BMPIDT
SBWLP:    CMP     (R3),ENCNOM
          BCS     PASTIT
          ADD     #68.,R3
          SOB     R2,SBWLP
          JMP     BMPIDT
;COME HERE WHEN HAVE FOUND ENCODER READING CORRESPONDING W/ AN L
PASTIT:   MOV     (R3),R4          ;GET THE JUST-FOUND POSITION
          SUB     -34.(R3),R4      ;COMPARE WITH PREV ENCODER READING
          BPL     CHKDP
          NEG     R4               ;TAKE ABS VALUE OF DIFFERENCE
CHKDP:    CMP     R4,DPLIM         ;SEE IF THERE'S A DISCONTINUITY HERE
          BLT     SAVIT            ;DATA OK. CONTINUE & SAVE A G VALUE
;COME HERE WHEN POSITION DATA @ (R3) AND -34.(R3) DISAGREE GREATLY.
;FIND OUT WHICH IS RIGHT AND PATCH THE OTHER:
          MOV     -34.(R3),R4
          SUB     -68.(R3),R4      ;SEE IF THE 2 PRIOR READINGS AGREE
          BPL     CNPTCH
          NEG     R4               ;TAKE ABS VALUE OF DIFFERENCE
CNPTCH:   CMP     R4,DPLIM         ;DO THEY AGREE?
          BPL     R3OK             ;NO. PATCH -34.(R3)
R3BAD:    MOV     -34.(R3),(R3)    ;YES. PATCH (R3)
          JMP     CKLTOR           ;RESUME SFWLP OR SBWLP
R3OK:     MOV     (R3),-34.(R3)    ;PATCH GOOD DATA INTO BAD
SAVIT:    MOV     R3,R4            ;COMPUTE ADDRESS OF G VALUE JUST FOUND
          SUB     #70.,R4          ;MAKE R4 POINT TO PRIOR SYNC
          ADD     R1,R4            ;NOW POINT TO G VALUE
          CLC                      ;COMPUTE AVERAGE OF CLOSEST NEIGHBORS:
          MOV     -68.(R4),R5
          ADD     68.(R4),R5
          ROR     R5
          MOV     R5,GAVE          ;GAVE=AVERAGE G
          SUB     (R4),R5          ;SEE IF CENTER VALUE CLOSE TO AVERAGE
          BPL     CHKDIF
          NEG     R5               ;TAKE ABS VALUE OF G(CENTER)-GAVE
CHKDIF:   CMP     R5,NOISLM        ;CLOSE ENOUGH SO CAN USE ALL 3 POINTS?
          BLE     USE3             ;YES
          JMP     REJECT           ;NO
;FIT WITH A+B*X+C*X**2:
USE3:     CMP     #5,SMOTH
          BEQ     D5
          CMP     #9.,SMOTH
          BEQ     D9
          MOV     -408.(R4),R5
          CLC
          ROR     R5
          MOV     R5,YM6
          MOV     408.(R4),R5
```

```
              CLC                                                     MAS     (R3)+,YP4
              ROR     R5                                              MOV     (R3)+,R4
              MOV     R5,YP6                                          MUL     YP4,R4
              MOV     -340.(R4),R5                                    ADD     R5,ACLO
              CLC                                                     ADC     R4
              ROR     R5                                              ADD     R4,ACHI
              MOV     R5,YM5                                     5    MAS     (R3),YM3
              MOV     340.(R4),R5                                     MOV     (R3),R4
              CLC                                                     MUL     YM3,R4
              ROR     R5                                              ADD     R5,ACLO
              MOV     R5,YP5                                          ADC     R4
D9:           MOV     -272.(R4),R5                                    ADD     R4,ACHI
              CLC                                                     MAS     (R3)+,YP3
              ROR     R5                                         10   MOV     (R3)+,R4
              MOV     R5,YM4                                          MUL     YP3,R4
              MOV     272.(R4),R5                                     ADD     R5,ACLO
              CLC                                                     ADC     R4
              ROR     R5                                              ADD     R4,ACHI
              MOV     R5,YP4                                     A5:  MAS     (R3),YM2
              MOV     -204.(R4),R5                                    MOV     (R3),R4
              CLC                                              15     MUL     YM2,R4
              ROR     R5                                              ADD     R5,ACLO
              MOV     R5,YM3                                          ADC     R4
              MOV     204.(R4),R5                                     ADD     R4,ACHI
              CLC                                                     MAS     (R3)+,YP2
              ROR     R5                                              MOV     (R3)+,R4
              MOV     R5,YP3                                          MUL     YP2,R4
D5:           MOV     -136.(R4),R5                              20    ADD     R5,ACLO
              CLC                                                     ADC     R4
              ROR     R5                                              ADD     R4,ACHI
              MOV     R5,YM2                                          MAS     (R3),YM1
              MOV     136.(R4),R5                                     MOV     (R3),R4
              CLC                                                     MUL     YM1,R4
              ROR     R5                                              ADD     R5,ACLO
              MOV     R5,YP2                                          ADC     R4
              MOV     -68.(R4),R5                               25    ADD     R4,ACHI
              CLC                                                     MAS     (R3)+,YP1
              ROR     R5                                              MOV     (R3)+,R4
              MOV     R5,YM1                                          MUL     YP1,R4
              MOV     68.(R4),R5                                      ADD     R5,ACLO
              CLC                                                     ADC     R4
              ROR     R5                                              ADD     R4,ACHI
              MOV     R5,YP1                                    30    MAS     (R3)+,Y0
              MOV     (R4),R5                                         MOV     (R3)+,R4
              CLC                                                     MUL     Y0,R4
              ROR     R5                                              ADD     R5,ACLO
              MOV     R5,Y0                                           ADC     R4
              MOV     (R3),R5                                         ADD     R4,ACHI
              SUB     -68.(R3),R5                                     MOV     ACHI,R4
              ASH     #7,R5                                     35    MOV     ACLO,R5
              MOV     R5,DT                                           DIV     (R3)+,R4
              MOV     ENCNOM,R4                                       MOV     R4,A
              SUB     -68.(R3),R4                              ;COMPUTE B:
              CLR     R5                                              CLR     ACHI
              DIV     DT,R4                                           CLR     ACLO
              ASH     #5,R4         ;2**14 MEANS X=1                  MOV     SMOTH,R2
              MOV     R4,X                                       40   DEC     R2
;COMPUTE A:                                                           ASR     R2
              MOV     R0,TEMP0                                        MOV     R2,R1
              MOV     R1,TEMP1                                        NEG     R1
              MOV     R2,TEMP2                                        CMP     #5,SMOTH
              MOV     R3,TEMP3                                        BEQ     B5
              CLR     ACHI                                            CMP     #9.,SMOTH
              CLR     ACLO                                            BEQ     B9
              MOV     #SMTBL,R3                                 45 B13: MAS    R1,YM6
              ADD     DISP,R3                                         MOV     R1,R4
              CMP     #5,SMOTH                                        MUL     YM6,R4
              BEQ     A5                                              ADD     R5,ACLO
              CMP     #9.,SMOTH                                       ADC     R4
              BEQ     A9                                              ADD     R4,ACHI
A13:          MAS     (R3),YM6                                        INC     R1
              MOV     (R3),R4                                    50   MAS     R2,YP6
              MUL     YM6,R4                                          MOV     R2,R4
              ADD     R5,ACLO                                         MUL     YP6,R4
              ADC     R4                                              ADD     R5,ACLO
              ADD     R4,ACHI                                         ADC     R4
              MAS     (R3)+,YP6                                       ADD     R4,ACHI
              MOV     (R3)+,R4                                        DEC     R2
              MUL     YP6,R4                                          MAS     R1,YM5
              ADD     R5,ACLO                                    55   MOV     R1,R4
              ADC     R4                                              MUL     YM5,R4
              ADD     R4,ACHI                                         ADD     R5,ACLO
              MAS     (R3),YM5                                        ADC     R4
              MOV     (R3),R4                                         ADD     R4,ACHI
              MUL     YM5,R4                                          INC     R1
              ADD     R5,ACLO                                         MAS     R2,YP5
              ADC     R4                                         60   MOV     R2,R4
              ADD     R4,ACHI                                         MUL     YP5,R4
              MAS     (R3)+,YP5                                       ADD     R5,ACLO
              MOV     (R3)+,R4                                        ADC     R4
              MUL     YP5,R4                                          ADD     R4,ACHI
              ADD     R5,ACLO                                         DEC     R2
              ADC     R4                                         B9:  MAS     R1,YM4
              ADD     R4,ACHI                                    65   MOV     R1,R4
A9:           MAS     (R3),YM4                                        MUL     YM4,R4
              MOV     (R3),R4                                         ADD     R5,ACLO
              MUL     YM4,R4                                          ADC     R4
              ADD     R5,ACLO                                         ADD     R4,ACHI
              ADC     R4                                              INC     R1
              ADD     R4,ACHI                                         MAS     R2,YP4
```

```
            MOV     R2,R4
            MUL     YP4,R4
            ADD     R5,ACLO
            ADC     R4
            ADC     R4
            ADD     YP5,R5
            ADC     R4
C9:         ADD     YM4,R5
            ADC     R4
            ADD     YP4,R5
            ADC     R4
            ADD     YM3,R5
            ADC     R4
            ADD     YP3,R5
            ADC     R4
C5:         ADD     YM2,R5
            ADC     R4
            ADD     YP2,R5
            ADC     R4
            ADD     YM1,R5
            ADC     R4
            ADD     YP1,R5
            ADC     R4
            ADD     Y0,R5
            ADC     R4
            MOV     R4,ACHI
            MOV     R5,ACLO
            MOV     SMOTH,R1
            NEG     R1
            MAS     R1,A
            MOV     R1,R4
            MUL     A,R4
            ADD     R5,ACLO
            ADC     R4
            ADD     R4,ACHI
            MOV     ACHI,R4
            MOV     ACLO,R5
            DIV     (R3),R4
            MOV     R4,C
            MOV     TEMP0,R0
            MOV     TEMP1,R1
            MOV     TEMP2,R2
            MOV     TEMP3,R3
;COMPUTE Y(X):
            MOV     A,YOFX
            MOV     B,R4
            MUL     X,R4
            ASHC    #2,R4
            ADD     R4,YOFX
            MOV     C,R4
            MUL     X,R4
            ASHC    #2,R4
            MUL     X,R4
            ASHC    #2,R4
            ADD     YOFX,R4
            MOV     R4,YOFX
STOREG:
            MUL     SCFAC,R4        ;MULT. BY NORM. FACTOR
            MOV     LTRY,R5
            DEC     R5
            ASL     R5
            ADD     R4,ACHI
            DEC     R2
            MAS     R1,YM3
            MOV     R1,R4
            MUL     YM3,R4
            ADD     R5,ACLO
            ADC     R4
            ADD     R4,ACHI
            INC     R1
            MAS     R2,YP3
            MOV     R2,R4
            MUL     YP3,R4
            ADD     R5,ACLO
            ADC     R4
            ADD     R4,ACHI
            DEC     R2
B5:         MAS     R1,YM2
            MOV     R1,R4
            MUL     YM2,R4
            ADD     R5,ACLO
            ADC     R4
            ADD     R4,ACHI
            INC     R1
            MAS     R2,YP2
            MOV     R2,R4
            MUL     YP2,R4
            ADD     R5,ACLO
            ADC     R4
            ADD     R4,ACHI
            DEC     R2
            MAS     R1,YM1
            MOV     R1,R4
            MUL     YM1,R4
            ADD     R5,ACLO
            ADC     R4
            ADD     R4,ACHI
            MAS     R2,YP1
            MOV     R2,R4
            MUL     YP1,R4
```

```
                ADD     R5,ACLO
                ADC     R4
                ADD     R4,ACHI
                MOV     ACHI,R4
                MOV     ACLO,R5
                DIV     (R3),R4
                MOV     R4,B
;COMPUTE C:
                CLR     R4
                CLR     R5
                CMP     #5,SMOTH
                BEQ     C5
                CMP     #9.,SMOTH
                BEQ     C9
C13:            MOV     YM6,R5
                ADD     YP6,R5
                ADC     R4
                ADD     YM5,R5
                ADD     CURGAD,R5
                MOV     R4,(R5)             ;STORE THE G VALUE
                ADD     LINC,LDUN(R0)
                CMP     LDUN(R0),LDNLIM     ;HAVE WE COMPUTED ALL 511 ELEMENTS?
                BNE     TRYNXT              ;NO. TRY TO COMPUTE NEXT ONE
                MOV     #-1,LDUN(R0)        ;YES. SET FLAG FOR THIS DETECTOR
                JMP     BMPIDT
;
REJECT:         MOV     -68.(R4),R5         ;CHECK DISCREPANCY BETWEEN NBRS
                SUB     68.(R4),R5
                BPL     CHKNBD
                NEG     R5                  ;GET ABS VALUE OF DIFFERENCE
CHKNBD:         CMP     R5,NOISLM           ;WITHIN NOISE TOLERANCE LIMIT?
                BGT     USE1                ;NO. USE ONLY 1 POINT
USE2:           MOV     GAVE,R4             ;YES. USE ONLY THE 2 NBRS
                BR      PRESTG
USE1:           MOV     (R4),R4
PRESTG:         CLC
                ROR     R4                  ;SCALE AS USE3 DOES
                JMP     STOREG
;
TRYNXT:         ADD     LINC,LTRY
                JMP     CMPNOM
;
;
;
BMPIDT:         INC     IDET
                CMP     IDET,#NDETS
                BGE     CONBMP
                JMP     DOADET
CONBMP:         CMP     LDUN,#-1            ;DETECTOR 1 DONE?
                BNE     CONT2
                CMP     LDUN+72,#-1         ;DETECTOR 30 DONE?
                BEQ     TRANDN              ;GO WRITE G DATA
;WAIT FOR IB3 TO FILL
CONT2:          WTSE$S  #3
                MOV     #3,-(SP)
                MOV     (PC)+,-(SP)
                .BYTE   41.,2
                EMT     ^O<377>
;
;
EF3:
;CHECK FOR I/O ERROR
                TSTIO$  SB3
                CMPB    SB3,#IS.SUC         ;TEST FOR SUCCESSFUL I/O
                BEQ     1$
                JSR     PC,ERR              ;ABORT IF I/O WAS BAD
;COPY UP IB2,IB3 CONTENTS INTO IB1,IB2
                MOV     #IB2,R0             ;SET INPUT POINTER
                MOV     #IB1,R1             ;SET OUTPUT POINTER
                MOV     #BYTSIB/16.,R2      ;COPY COUNTER
CPUPLP:         .REPT   16.
                MOV     (R0)+,(R1)+         ;COPY 1 WORD
                .ENDM
                MOV     (R0)+,(R1)+         ;COPY 1 WORD
                MOV     (R0)+,(R1)+         ;COPY 1 WORD
                MOV     (R0)+,(R1)+         ;COPY 1 WORD
                MOV     (R0)+,(R1)+         ;COPY 1 WORD
                MOV     (R0)+,(R1)+         ;COPY 1 WORD
                MOV     (R0)+,(R1)+         ;COPY 1 WORD
                MOV     (R0)+,(R1)+         ;COPY 1 WORD
                MOV     (R0)+,(R1)+         ;COPY 1 WORD
                MOV     (R0)+,(R1)+         ;COPY 1 WORD
                MOV     (R0)+,(R1)+         ;COPY 1 WORD
                MOV     (R0)+,(R1)+         ;COPY 1 WORD
                MOV     (R0)+,(R1)+         ;COPY 1 WORD
                MOV     (R0)+,(R1)+         ;COPY 1 WORD
                MOV     (R0)+,(R1)+         ;COPY 1 WORD
                MOV     (R0)+,(R1)+         ;COPY 1 WORD
                SOB     R2,CPUPLP
;
                CMP     BFSRQD,#BFSTRN
                BEQ     FNDSYN              ;IF LAST, DON'T ASK FOR MORE
;ASK FOR A NEW IB3 FILL WHILE COMPUTING FROM IB1,IB2
                QIO$S   #IO.RLB,#DK1,#3,,#SB3,,<#IB3,#BYTSIB,,#0,INPSEC>,ERR
                CLR     -(SP)
                MOV     INPSEC,-(SP)
                CLR     -(SP)
                CLR     -(SP)
                MOV     #BYTSIB,-(SP)
```

```
            MOV      #IB3,-(SP)
            CLR      -(SP)
            MOV      #SB3,-(SP)
            CLR      -(SP)
            MOVB     #3,(SP)
            MOV      #DK1,-(SP)
            MOV      #IO.RLB,-(SP)
            MOV      (PC)+,-(SP)
            .BYTE    1,12.
            EMT      ^O<377>
            BCC      .+6
            JSR      PC,ERR
            INC      BFSRQD
            ADD      #SEXIBF,INPSEC
;
FNDSYN:
;FIND SYNC FOR DATA IN IB2
            MOV      #IB2,R4
            JSR      PC,FSYNC
;CONVERT DETECTOR READINGS IN IB2 TO MU SUMS
            JMP      DECOM              ;COMPUTE SOME MORE G VALUES
;
;
TRANDN:
;COME HERE WHEN HAVE COMPUTED ALL NSPSAM VALUES FOR ALL NDETS DETECTORS.
;CHECK FOR I/O ERROR ON LAST WRITE, IF THERE WAS ONE
            TST      TRNSDN             ; IS THIS THE 1ST TRANSLATION?
            BEQ      WRITCS             ;SKIP I/O TEST IF IT IS
            TSTIO$   SB4
            CMPB     SB4,#IS.SUC        ;TEST FOR SUCCESSFUL I/O
            BEQ      1$
            JSR      PC,ERR             ;ABORT IF I/O WAS BAD
;WRITE NDETS G ARRAYS TO DISK
WRITCS: QIO$$       #IO.WLB,#DK1,#4,,#SB4,,<#0B,#BYTSOB,,#0,OUTSEC>,ERR
            CLR      -(SP)
            MOV      OUTSEC,-(SP)
            CLR      -(SP)
            CLR      -(SP)
            MOV      #BYTSOB,-(SP)
            MOV      #0B,-(SP)
            CLR      -(SP)
            MOV      #SB4,-(SP)
            CLR      -(SP)
            MOVB     #4,(SP)
            MOV      #DK1,-(SP)
            MOV      #IO.WLB,-(SP)
            MOV      (PC)+,-(SP)
            .BYTE    1,12.
            EMT      ^O<377>
            BCC      .+6
            JSR      PC,ERR
            ADD      #OSXTRN,OUTSEC
            INC      TRNSDN
            CMP      TRNSDN,#NTRANS
            BEQ      CLNUP              ;QUIT IF HAVE DONE ALL TRANSLATIONS
            JMP      DOTRAN             ;ELSE DO NEXT
;
;
CLNUP:  WTSE$$      #4
            MOV      #4,-(SP)
            MOV      (PC)+,-(SP)
            .BYTE    41.,2
            EMT      ^O<377>
;
;CHECK FOR I/O ERROR
            TSTIO$   SB4
            CMPB     SB4,#IS.SUC        ;TEST FOR SUCCESSFUL I/O
            BEQ      1$
            JSR      PC,ERR             ;ABORT IF I/O WAS BAD
;REQUEST STARTUP OF MGP
            RQST$$   MGPNAM
            CLR      -(SP)
            CLR      -(SP)
            CLR      -(SP)
            CLR      -(SP)
            MOV      MGPNAM,-(SP)
            MOV      @(SP),-(SP)
            ADD      #2,2(SP)
            MOV      @2(SP),2(SP)
            MOV      (PC)+,-(SP)
            .BYTE    11.,7
            EMT      ^O<377>
;
            EXIT$$
            MOV      (PC)+,-(SP)
            .BYTE    51.,1
            EMT      ^O<377>
;THE END
;
SUBROUTINE TO CONVERT 2 DIGIT DECIMAL # TO ASCII
ONV2D:
            CLR      R4
            DIV      #10.,R4
            ADD      #260,R4
            ADD      #260,R5
            SWAB     R5
            ADD      R4,R5
            RTS      PC
```

```
SUBROUTINE TO OUTPUT MESSAGE LINE:
RINT:   QIO$S   #IO.WLB,#TM,#10.,,#IOSTB,,<#MES,#24.,#040>
        CLR     -(SP)
        CLR     -(SP)
        CLR     -(SP)
        MOV     #049,-(SP)
        MOV     #24.,-(SP)
        MOV     #MES,-(SP)
        CLR     -(SP)
        MOV     #IOSTB,-(SP)
        CLR     -(SP)
        MOVB    #10.,(SP)
        MOV     #TM,-(SP)
        MOV     #IO.WLB,-(SP)
        MOV     (PC)+,-(SP)
        .BYTE   1,12.
        EMT     ^O<377>
        WTSE$S  #10.
        MOV     #10.,-(SP)
        MOV     (PC)+,-(SP)
        .BYTE   41.,2
        EMT     ^O<377>
        CMPB    #IS.SUC,IOSTB
        BEQ     70$
        JSR     PC,ERR
)$:
        RTS     PC

SUBROUTINE TO CONVERT AND STORE OCTAL # AS ASCII
:TASC:  CLR     R4
        ASHC    #1,R4
        ADD     #260,R4
        MOVB    R4,(R3)+
        MOV     #5,DIGCNT
\LOOP:  CLR     R4
        ASHC    #3,R4
        ADD     #260,R4
        MOVB    R4,(R3)+
        DEC     DIGCNT
        BNE     OALOOP
        RTS     PC

SUBROUTINE TO FIND 1ST SYNC WORD IN BUFFER STARTING @ (R4)
RETURNS WITH R4 POINTING TO 1ST SYNC WORD IN BUFFER
SYNC:   ADD     #68.,R4
SYNTST: TST     (R4)+
        BNE     SYNTST
        DEC     R4
        DEC     R4
        RTS     PC
;
;
;
;
ERR:    MOV     $DSW,R0         ;PICK UP DIRECTIVE STATUS WORD
        MOV     (SP)+,R1        ;AND CALLING ADDRESS
        HALT
;
;
MGPNAM: .WORD   MGP
MGP:    .RAD50  /MGP /
;
;
LTOR:   .WORD   0
LINC:   .WORD   0
LDNLIM: .WORD   0
BFSRQD: .WORD   0
TRNSDN: .WORD   0
INPSEC: .WORD   0
IDET:   .WORD   0
LTRY:   .WORD   0
ENCNOM: .WORD   0
FRSTPO: .WORD   0
LASTPO: .WORD   0
CURGAD: .WORD   0
OUTSEC: .WORD   0
;
DT:     .WORD   0
;DATA POINTS AROUND ENCNOM:
YM6:    .WORD   0
YM5:    .WORD   0
YM4:    .WORD   0
YM3:    .WORD   0
YM2:    .WORD   0
YM1:    .WORD   0
Y0:     .WORD   0
YP1:    .WORD   0
YP2:    .WORD   0
YP3:    .WORD   0
YP4:    .WORD   0
YP5:    .WORD   0
YP6:    .WORD   0
;DBL ACCUM:
ACHI:   .WORD   0
ACLO:   .WORD   0
;COEFFICIENTS FOR POLYNOMIAL FIT:
A:      .WORD   0
B:      .WORD   0
C:      .WORD   0
```

```
;
X:      .WORD   0
YOFX:   .WORD   0
;TABLE OF BYTE OFFSETS IN DATA FRAMES:
;VALUE = # OF BYTES PAST SYNC WORD ADDRESS
FRINDT: .WORD   4
        .WORD   6
        .WORD   8.
        .WORD   10.
        .WORD   12.
        .WORD   14.
        .WORD   16.
        .WORD   18.
        .WORD   20.
        .WORD   22.
        .WORD   24.
        .WORD   26.
        .WORD   28.
        .WORD   30.
        .WORD   32.
        .WORD   38.
        .WORD   40.
        .WORD   42.
        .WORD   44.
        .WORD   46.
        .WORD   48.
        .WORD   50.
        .WORD   52.
        .WORD   54.
        .WORD   56.
        .WORD   58.
        .WORD   60.
        .WORD   62.
        .WORD   64.
        .WORD   66.
;
;TABLE OF TIME OFFSETS FOR DETECTORS
;UNITS ARE SUB-FRAME INTERVALS (1/34TH OF NOMINALLY 1 MSEC FRAME TIME)
;TIMES ARE RELATIVE TO TIME OF 1ST POSITION MEASUREMENT IN FRAME
DOFFT:  .WORD   1
        .WORD   2
        .WORD   3
        .WORD   4
        .WORD   5
        .WORD   6
        .WORD   7
        .WORD   8.
        .WORD   9.
        .WORD   10.
        .WORD   11.
        .WORD   12.
        .WORD   13.
        .WORD   14.
        .WORD   15.
        .WORD   18.
        .WORD   19.
        .WORD   20.
        .WORD   21.
        .WORD   22.
        .WORD   23.
        .WORD   24.
        .WORD   25.
        .WORD   26.
        .WORD   27.
        .WORD   28.
        .WORD   29.
        .WORD   30.
        .WORD   31.
        .WORD   32.
;
;
;
LDUN:   .BLKW   NDETS
SB2:    .BLKW   2
SB3:    .BLKW   2
SB4:    .BLKW   2
;
;ARGUMENT LIST FOR FORTRAN SUBROUTINE CETABS
ARGLST: .BYTE   7,0
        .WORD   IA
        .WORD   IOFF
        .WORD   ISA
        .WORD   IFA
        .WORD   ITO
        .WORD   ND
        .WORD   LPI
;
;
SMTBL:  -3
        12.
        17.
        35.
        10.
        -11.
        0
        9.
        16.
        21.
        24.
        25.
```

```
                    143.
                    182.
                    -21.
                     14.
                     39.
                     54.
                     59.
                    231.
                     60.
        SMOTH:  .BLKB    2
        DISP:   .WORD    0
        IOSTB:  0,0
        PMSG:   .ASCII/*=/
                .EVEN
        TEMP0:  .WORD    0
        TEMP1:  .WORD    0
        TEMP2:  .WORD    0
        TEMP3:  .WORD    0
        ;
        ;
        IA:     .WORD    0
        IOFF:   .WORD    0
        ISA:    .WORD    0
        TAUSF:  .WORD    0
        FACTOR: .WORD    0
        NOISLM: .WORD    0
        DPLIM:  .WORD    0
        IFA:    .WORD    0
        ITO:    .WORD    0
        ;
        ;
        ;*****************************************************************
        ND:     .WORD    NDETS
        LPI:    .WORD    ENCLPI
        NCANDS: .WORD    NFRMS          ;# OF FRAMES TO SEARCH FOR POSITION
        GAVE:   .WORD    0
        DENCPF: .WORD    0              ;ENCODER CHANGE PER FRAME
        HAFDEN: .WORD    0              ;1/2 THE ENCODER CHANGE PER FRAME
        ENCADJ: .WORD    0              ;ADJUSTMENT FOR NET TIME OFFSET FOR DET
        SCFAC:  .WORD    0
        MES:    .ASCII  / T/
        MES0:   .ASCII  /**/
        MES1:   .ASCII  / S/
040     MES2:   .ASCII  /YN /

040     MES3:   .ASCII  /        /
040

040     MES4:   .ASCII  /        /
040
        ;
        SPACES: .ASCII  / S/
        YN:     .ASCII  /YN/
        SPACEE: .ASCII  / E/
        NC:     .ASCII  /NC/
        ACLIM:  .WORD    4
        SPACED: .ASCII  / D/
        FRSTD:  .WORD    0
        DET:    .WORD    0
        DIGCNT: .WORD    0
        ;
        RCPBUF:
        IB1:    .BLKB    BYTSIB
        IB2:    .BLKB    BYTSIB
        IB3:    .BLKB    BYTSIB
        ;
        OB:     .BLKB    BYTSOB
        ;
        ;
                .PSECT   ICEN,GBL,OVR,D
        ICEN:
                .PSECT
        ;
        C CETABS
        C SUBROUTINE TO COMPUTE ENCODER VALUES TABLES FOR MG
        C TABLES ARE PROGRAM SECTIONS OF MG
        C 10/29/75, TRL
0001            SUBROUTINE CETABS(IA,IOFF,ISA,IFA,ITO,ND,LPI)
0002            COMMON /ICEN/ICEN(30)
0003            COMMON /IDIF/IDIF(30)
        C IA=# OF MICRONS PER SPATIAL SAMPLE INTERVAL
        C IOFF=ENCODER READING WHEN YOKE CENTERED OVER AXIS
        C ISA=SOURCE-AXIS DISTANCE IN .1MM UNITS
        C IFA=TOTAL FAN ANGLE IN MILLIDEGREES
        C ITO=THETA OFFSET IN MILLIDEGREES
        C ND=# OF DETECTORS
        C LPI=LINES PER INCH OF ENCODER
        C ICEN=TABLE OF CENTER ENCODER VALUES VS DETECTOR
        C IDIF=TABLE OF DIFFERENTIAL ENCODER VALUES VS DETECTOR
        C IDIFSH=SHIFT COUNT FOR IDIF VALUES (MUST AGREE WITH MG)
        C

C
        C
0004            DATA IDIFSH/7/
```

```
0005        DATA PI/3.1415926536/
0006        FACTOR=FLOAT(2**IDIFSH)
0007        DSAXCM=FLOAT(ISA)/100.
0008        DELTHR=((FLOAT(IFA)/1000.)/FLOAT(ND))*PI/180.
0009        THTOFF=(FLOAT(ITO)/1000.)*PI/180.
0010        ENCLCM=FLOAT(LPI)/2.540
0011        ACM=FLOAT(IA)/10000.
0012        DO 100 I=1,ND
0013        THETRD=.5*DELTHR*FLOAT(2*I-ND-1)+THTOFF
0014        ICEN(I)=-IFIX(DSAXCM*ENCLCM*SIN(THETRD)/COS(THETRD))+IOFF
0015        IDIF(I)=IFIX(FACTOR*ACM*ENCLCM/COS(THETRD))
0016  100   CONTINUE
0017        RETURN
0018        END
```

CORE=,                                                                  ,LP/SP=SETREC

```
C SETREC
C PROGRAM TO RECORD SCAN PARAMETERS FOR PROJECTIONS PROGRAM(MC).
C PARAMETERS ARE STORED AS FILE RECP.DAT.
C
C STRUCTURE OF RECP ARRAY STORED FOR MC:
C  WORD   VARIABLE              PARAMETERS
C   1     IA        SPATIAL SAMPLE INTERVAL (764 = .5 MM)
C                     (USE 1750 FOR BODY SCANS)
C   2     IOFF      LINEAR ENCODER OFFSET
C                     (READING WHEN YOKE CENTERED ON AXIS)
C   3     ISA       DISTANCE FROM XRAY SOURCE
C                     (FOCAL SPOT CENTER) TO AXIS
C   4     TAUSF     TIME DELAY,IN SUB-FRAME INTERVALS,SAMPLE TIME
C                     TO READOUT (UNITS ARE 1/34. MSEC)
C   5     FACTOR    SCALE FACTOR TO NORMALIZE C VALUES
C                     (FACTOR = OCTAL 57500 TO MAKE F(WATER)=1000.)
C   6     NOISLM    NOISE LIMIT
C                     (IN RAW C VALUES)
C   7     DPLIM     PERMISSABLE CHANGE IN ENCODER/.5 MSEC
C
C   8     IFA       TOTAL FAN ANGLE
C                     (UNITS ARE 1/1000 DEGREE)
C   9     ITO       CORRECTION FOR NON-PLUMB BEAM
C
C
C
C
C INITIALIZE PARAMETERS
0001        INTEGER RECP(9)
0002        CALL ASSIGN(1,'RECP.DAT;1')
C INPUT PARAMETERS FROM USER
0003        WRITE(6,10)
0004  10    FORMAT('$IA=')
0005        READ(5,12)RECP(1)
0006  12    FORMAT(I7)
0007        WRITE(6,20)
0008  20    FORMAT('$ IOFF=')
0009        READ(5,12)RECP(2)
0010        WRITE(6,30)
0011  30    FORMAT('$ ISA=')
0012        READ(5,12)RECP(3)
0013        WRITE(6,40)
0014  40    FORMAT('$ TAUSF=')
0015        READ(5,12)RECP(4)
0016        WRITE(6,50)
0017  50    FORMAT('$ FACTOR=')
0018        READ(5,12)RECP(5)
0019        WRITE(6,60)
0020  60    FORMAT('$.NOISLM=')
0021        READ(5,12)RECP(6)
0022        WRITE(6,70)
0023  70    FORMAT('$ DPLIM=')
0024        READ(5,12)RECP(7)
0025        WRITE(6,80)
0026  80    FORMAT('$ IFA=')

0027        READ(5,12)RECP(8)
0028        WRITE(6,90)
0029  90    FORMAT('$ ITO=')
0030        READ(5,12)RECP(9)
C WRITE FILE
0031        WRITE(1)RECP
0032        ENDFILE 1
0033        END
```

I claim:

1. A method for producing radiation transmission data signals in a computed tomography system of the type wherein one or more radiation source and detection units move about a body undergoing examination with velocity profiles which may vary with time; comprising the steps of:

sampling and storing radiation detector output signals and detector position signals from each of said detectors at a large number of sample points which are uniformly separated in time;

associating sets of said sample points with projection positions which are uniformly separated in space; and interpolating values of radiation detector output signals from the sample points in each of said sets to obtain low-pass-filtered signals representative of radiation transmission values at said projection positions.

2. The method of claim 1 wherein the number of sample points is larger than the number of projection positions.

3. The method of claim 2 wherein the interpolating step includes fitting the detector output signal to a polynomial curve and estimating the values of said filtered signals from the equation of said curve.

4. The method of claim 3 wherein each of the sets comprises the five sample points; $y_{-2}, y_{-1}, y_0, y_1,$ and $y_2$; which are closest in space to the desired projection position.

5. The method of claim 4 wherein the said polynomial curve has the equation $a + bx + cx^2$ wherein the coefficients a, b and c are determined to provide a least-squares curve fit.

6. The method of claim 5 wherein the coefficients are determined from the formulae: $a = 1/35(-3y_{-2} + 12y_{-1} + 17y_0 + 12y_1 - 3y_2)$; $b = 1/10(-2y_{-2} - y_{-1} + y_1 + 2y_2)$; and $c = 1/10(y_{-2} + y_{-1} + y_0 + y_1 + y_2 - 5a)$.

7. The method of claim 3 wherein the signals representative of radiation transmission values at said projection points are processed with a convolution-backprojection algorithm to calculate tomographic image information.

8. In a computed tomography system of the type which includes scanning means for successively moving radiation transmission measurement components about an object, data sampling means connected to successively sample signals from said scanning means which are representative of the radiation transmission characteristics of said objects along each of a first set of spatially distinct transmission paths, and imaging means connected to receive said signal samples from said data sampling means and to compute tomographic image data therefrom, the improvement wherein:

said data sampling means function to sample signals from said scanning means at regular intervals in time; and further including means, associated with said imaging means, which function to receive said sampled signals from said data transmission and sampling means and to interpolate sets of said sampled signals to produce therefrom sets of calculated projection signals which are representative of the transmission characteristics of said object along a second set of transmission paths which are uniformly distributed in space, said projection signals being further processed by said imaging means to calculate said tomographic image data.

9. The improvement of claim 8 wherein said data sampling means further include means for sampling signals representative of the physical position of components in said scanning means.

10. The improvement of claim 9 wherein said data sampling means function to produce a greater number of said sampled signals than the number of unknown quantities which are required to produce a closed solution of simultaneous equations which relate said image data to said transmission measurements.

11. The improvement of claim 10 wherein said number of samples in from five times greater to ten times greater than said number of unknowns.

12. The improvement of claim 9 wherein each set of said sampled signals includes at least those five signals which are sampled along paths that are spatially closest to an associated transmission path in said second set.

13. The improvement of claim 8 wherein said means associated with said image means function to interpolate said sets of sampled signals by fitting a high order function to said signals in said sets and interpolating said high order function.

14. The improvement of claim 13 wherein said high order function is a quadratic function having the equation $a + bx + cx^2$.

15. The improvement to claim 14 wherein each of said sets includes five points, $y_{-2}, y_{-1}, y_0, y_1$ and $y_2$, and wherein the coefficients of said quadratic equation is determined by the formula $a = 1/35(-3y_{-2} + 12y_{-1} + 17y_0 + 12y_1 - 3y_2)$; $b = 1/10(-2y_{-2} - y_1 + y_1 + y_1 + 2y_2)$ and $c = 1/10(y_{-2} + y_{-1} + y_0 + y_1 + y_2 - 5a)$.

16. The improvement of claim 13 wherein said curve fit is a least-squares curve fit.

* * * * *

UNITED STATES PATENT AND TRADEMARK OFFICE
CERTIFICATE OF CORRECTION

PATENT NO. : 4,136,388
DATED : January 23, 1979
INVENTOR(S) : THOMAS R. LINDQUIST It is certified that error appears in the above—identified patent and that said Letters Patent are hereby corrected as shown below:

Column 32, line 38, (Claim 15, line 5) should be:

-- $+ 17y_0 + 12y_1 - 3y_2$); $b = 1/10$ ($-2y_{-2} - y_{-1} + y_1$ --

Signed and Sealed this

Fifth Day of June 1979

[SEAL]

Attest:

RUTH C. MASON
Attesting Officer

DONALD W. BANNER
Commissioner of Patents and Trademarks